(12) United States Patent
Pienaar et al.

(10) Patent No.: US 8,558,038 B2
(45) Date of Patent: Oct. 15, 2013

(54) EPOXIDATION OF GLYCEROL AND DERIVATIVES THEREFROM

(75) Inventors: Andre Pienaar, Pretoria (ZA); Laurence Justin Pienaar Wilson, Midrand (ZA); Michael Stockenhuber, Callaghan (AU)

(73) Assignee: AEL Mining Services Limited, Sandton (ZA)

( * ) Notice: Subject to any disclaimer, the term of this patent is extended or adjusted under 35 U.S.C. 154(b) by 0 days.

(21) Appl. No.: 13/700,380

(22) PCT Filed: Jun. 21, 2011

(86) PCT No.: PCT/ZA2011/000041
§ 371 (c)(1),
(2), (4) Date: Nov. 27, 2012

(87) PCT Pub. No.: WO2012/003519
PCT Pub. Date: Jan. 5, 2012

(65) Prior Publication Data
US 2013/0090497 A1    Apr. 11, 2013

(30) Foreign Application Priority Data

Jun. 29, 2010    (ZA) .................. 2010/04585

(51) Int. Cl.
*C07C 205/00*     (2006.01)
*B01F 17/00*      (2006.01)

(52) U.S. Cl.
USPC .................... 568/944; 516/9; 516/76

(58) Field of Classification Search
USPC ........................ 568/944; 516/9, 76
See application file for complete search history.

(56) References Cited

U.S. PATENT DOCUMENTS

2009/0239958 A1*   9/2009   Sakanishi et al. ................. 516/9

* cited by examiner

*Primary Examiner* — Jafar Parsa
(74) *Attorney, Agent, or Firm* — Michael Best & Friedrich LLP

(57) ABSTRACT

A method producing a surfactant from glycerol by converting glycerol, in a first step, to glycidol, polymerizing glycidol to an aliphatic alcohol and finally substituting a hydroxyl group with a substitute anion.

21 Claims, No Drawings

EPOXIDATION OF GLYCEROL AND DERIVATIVES THEREFROM

BACKGROUND OF THE INVENTION

This invention relates generally to explosive compositions and intermediate compounds for use in an explosive composition and more specifically to explosive compositions and intermediate compounds derived from glycerol.

Trinitro-based explosives, so-called first generation explosives, for example trinitroglycerine (NG) and trinitrotoluene (TNT), are powerful "high" explosives. However the biggest mark against their use is their relative thermodynamic instability, and their tendency to spontaneously explode, which make these explosives unsafe to handle. What distinguishes these explosives over later generations of explosives is the presence of a fuel and an oxidant on the same molecule i.e. the hydrocarbon skeleton providing the fuel and nitrate moieties providing the oxidant.

Emulsion explosives are a later generation of explosives which are ammonium nitrate (AN) based and are currently widely used in civil applications. These explosives however exhibit relatively slower reaction rates when compared to the aforementioned high explosives.

An emulsion explosive typically comprises an oxidant, a carbonaceous fuel, such as diesel (the AN and fuel oil mixture is termed ANFO), and a surfactant. The oxidant, usually ammonium nitrate ($NH_4NO_3$), supplies oxygen atoms to the fuel, usually a hydrocarbon compound, such that the fuel can be oxidized to carbon dioxide ($CO_2$) and water ($H_2O$) in a rapid exothermic reaction.

Emulsion explosives typically comprise a continuous organic or major phase (e.g. the carbonaceous fuel) and a discontinuous aqueous or minor phase containing the oxidant (e.g. AN). With the separation of the oxidant and the fuel in two phases, these explosives are relatively easily handled but this comes at a cost of a relative loss of explosive power.

An advantage to the use of emulsion explosives is that the base emulsion is non detonable. Base emulsion typically has a density greater than 1.3 g/cm³. At this density the emulsion will not detonate. The emulsion needs to be sensitized by the addition of a sensitizing agent such as micro balloons or sodium nitrite. This will reduce the density of the emulsion to around 1.0 g/cm³. During the sensitizing process, small voids are introduced to the emulsion which act as hot spots during initiation, leading to detonation.

Since AN does not dissolve in hydrocarbons but is highly soluble in water, and to provide for a large contact surface between the oxidant and the fuel, the AN solution is emulsified in the hydrocarbon. Emulsification occurs with the introduction of a surfactant (emulsifier), one of several types, and intense stirring. An emulsion explosive can therefore be described as a highly concentrated AN solution dispersed in the hydrocarbon as droplets, having a diameter ranging from 0.01 to 10 μm, with the surfactant in the interface between the hydrocarbon and each AN solution droplet.

A surfactant, in this context, is not only an essential component to an emulsion explosive but it also provides a secondary fuel source in the composition.

It is conventional for surfactants, made for this application, to be manufactured with the aid of emulsifiers based on sugar esters. More recently polyisobutylene succinic anhydride (PIBSA) based surfactants have found increasing use in this application as they generally result in more stable emulsions. Also PIBSA is amenable to processing which allows for the manufacture of a wide range of PIBSA based surfactants, each one engineered for a particular explosive application, especially with regards to shelf life, viscosity and cost.

Whilst emulsion explosives have many advantages in the civil context, several negative economic and environmental factors associated with the component compounds of these explosives, i.e. PIBSA, AN, and carbonaceous fuels, weigh against their use. As PIBSA is manufactured from mineral oils, it is inexorably tied to crude oil, its fluctuating availability and cost. Coupled to this factor are the environmental issues associated with crude oil production. With regards to AN, it is currently in short supply worldwide.

From the aforegoing it is clear that there is a need for an explosive composition which has component compounds which are manufactured from raw and intermediate materials, which are readily and cheaply available, which are relatively easily transported and handled in situ, which have a relatively low environmental impact and which have high explosive power akin to the first generation explosives.

The invention at least partially addresses the aforementioned problems.

SUMMARY OF INVENTION

The term "surfactant" is used herein to describe an organic compound that exhibits an amphiphilic characteristic, meaning it is both hydrophobic and hydrophilic, containing both a hydrophobic group, usually a hydrocarbon chain in the case of an aliphatic compound, hereinafter referred to as "a tail group", and a hydrophilic moiety attached to the tail group, hereinafter referred to as "a head group".

The term "leaving group" refers to an ion or substituent moiety which has the ability to detach itself from a molecule, thereby being replaced on the molecule with another moiety.

A "polyol" is a compound with multiple hydroxyl functional groups (moieties) available for organic reactions.

The term "epoxide" is used herein to describe a compound containing at least one oxygen atom bridged on a carbon-carbon bond and the term epoxidizing refers to the process of forming an epoxide, for example glycidol, from a precursor compound.

The invention provides a method of producing a surfactant from glycerol which includes the steps of:
(a) converting glycerol to glycidol,
(b) polymerizing glycidol (the monomer) to produce an aliphatic alcohol (the polymer) with molecular formula $C_nH_{(2n)}O$, wherein n is a numerical integer in the range 5 to 25; and
(c) substituting the hydroxyl moiety of the alcohol with a suitable head group.

The conversion of glycerol to glycidol may include the additional intermediate steps of dehydrating glycerol to acrolein (propenal), hydrogenating acrolein to allyl alcohol and epoxidizing allyl alcohol, with hydrogen peroxide, to glycidol.

An acidic catalyst, for example a zeolite, may be used in the dehydration step.

In the hydrogenation step, a hydrogenating catalyst may be used. The catalyst may include a support, of a suitable material providing a high surface area to volume, and at least one transition metal on the support. The transition metal may be cadmium, silver or iron. The support may be silica or alumina.

An epoxidzing catalyst may be used in the epoxidizing step. The epoxidizing catalyst may be a titanium molecular sieve, for example TS-1, or a gold containing catalyst.

Polymerization may take place by heating glycidol, in an acidic medium, for a predetermined period, the length of which is dependent upon the number of carbon atoms (n) required in a tail group of the surfactant.

The polymerization process may be initiated with a suitable initiator, for example boron triflouride.

Preferably the tail group has a length i.e. the number of carbon atoms (n) present, in a range n=10 to 20. Should the chain length increase much above n=20, the resultant surfactant product will be increasingly viscous with concomitant detonation setbacks and the need to add a diluent. Should the chain length be less than n=10, there is an increased tendency for the surfactant to crystallize.

The head group may be an anionic moiety, for example any one of the following: a carboxylate, a sulphate, a sulphonate, a phosphate and salts thereof.

Alternatively, the head group may be a nonionic moiety such as, for example, urea, MEA, amide, imide or any other suitable function group.

A urea moiety may be substituted for the hydroxyl moiety in step (c) by heating the alcohol in the presence of an equimolar amount of urea.

The invention also provides, in another aspect, a method of producing an explosive compound from glycerol which includes the steps of:
(a) converting glycerol to glycidol;
(b) polymerizing glycidol (the monomer) to produce an aliphatic polyol the polymer) with molecular formula $C_xH_{(2X+2)}O_Y$, wherein X and Y are numerical integers in the range 3 to 30 and 3 to 15 respectively;
(c) activating the aliphatic polyol by substituting the polyol's hydroxyl moieties with a suitable leaving group to form an activated intermediate; and
(d) nitrating the activated intermediate to substitute each of the leaving groups with a nitrate moiety to produce the explosive compound.

The conversion of glycerol to glycidol may include the additional intermediate steps of dehydrating glycerol to acrolein (propenal), hydrogentating acrolein to allyl alcohol and epoxidizing allyl alcohol, with hydrogen peroxide, to glycidol.

An acidic catalyst, for example a zeolite, may be used in the dehydration step.

In the hydrogenation step, a hydrogenating catalyst may be used. The catalyst may include a support, of any suitable material with a high surface area to volume ratio, and at least one transition metal on the support. The transition metal may be cadmium, silver or iron. The support may be silica or alumina.

An epoxidzing catalyst may be used in the epoxidizing step. The epoxidizing catalyst may be a titanium molecular sieve, for example TS-1, or a gold containing catalyst.

Preferably, the aliphatic polyol is 1,2,4,6 heptanetetrol ($C_7H_{16}O_4$) and preferably three of the four hydroxyl moieties are substituted with a suitable leaving group in step (c).

A suitable leaving group may be any one of the following: chloride, iodide, bromide, azide ($N_3^-$), thiocyanate ($SCN^-$) and nitro ($NO_2$).

Preferably the leaving group is a chloride ion and the aliphatic polyol is activated with chloride by bubbling chlorine gas through a solution of the polyol in a chlorination process. In this case, the activated intermediate is 2,4,6 trichloroheptane.

The nitration step (d) may include the addition of a nitrate salt, for example sodium nitrate, to the activated intermediate. This step may be performed in situ.

Preferably the explosive compound is 2,4,6 trinitroheptane.

DESCRIPTION OF PREFERRED EMBODIMENT

A surfactant, for use in an emulsion explosive, is produced in a first aspect of the invention using glycerol, which is produced as waste product from the synthesis of bio-fuels and is a readily and cheaply available feedstock for the production of the surfactants.

A general reaction sequence for the production of an aliphatic alcohol intermediate from glycerol in the manufacture of a surfactant is illustrated in Diagram 1.

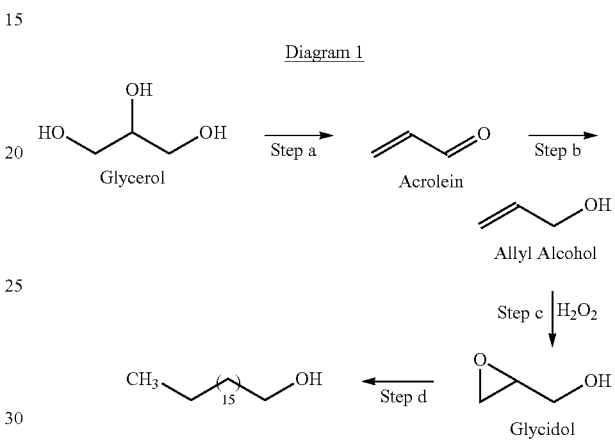

Diagram 1

In step (a), glycerol is dehydrated to acrolein (propenal), an unsaturated aldehyde, aided by an acidic catalyst, such as a zeolite catalyst, for example H-ZSM5.

In step (b) acrolein is hydrogenated to allyl alcohol over a transition metal catalyst, which includes, for example, one or more of cadmium, silver or iron supported on a silica or alumina support.

In step (c) allyl alcohol is epoxidized, with hydrogen peroxide, over a titanium molecular sieve catalyst, for example TS-1, or a gold containing catalyst, to form glycidol.

In step (d), glycidol, as a monomer in this part of the reaction, is polymerized to an aliphatic alcohol, initiated by boron triflouride, which is the resultant polymer in this polymerization reaction.

The aliphatic alcohol, depending on the reaction conditions and particularly the duration of the polymerization reaction, can have a carbon chain length (n) of between 5 and 25, preferably between 10 and 20. Therefore by altering the reaction parameters of step (b), a range of aliphatic alcohols, with differing carbon chain lengths, can be produced. Generally, the longer the carbon chain length, the more viscous the resultant surfactant. The shorter the carbon chain length, the greater the tendency for the resultant surfactant to crystallize, a detrimental occurrence for a surfactant in an emulsion explosive composition.

Depending on requirement, an alcohol of a particular chain length can be chosen and fed into a second stage in the surfactant production process (explained below) to produce a surfactant tailor-made for a particular application. Flexibility in the surfactant production process is therefore created.

Diagram 2 illustrates, by way of two divergent examples, the second stage of surfactant production. The aliphatic alcohol product of the first stage process described above undergoes substitution reaction whereby the hydroxyl moiety of the alcohol is replaced with a suitable head group. The choice of a head group is once again dependent on application. With a range of head groups available for substitution, the flexibility of the surfactant production process is multiplied.

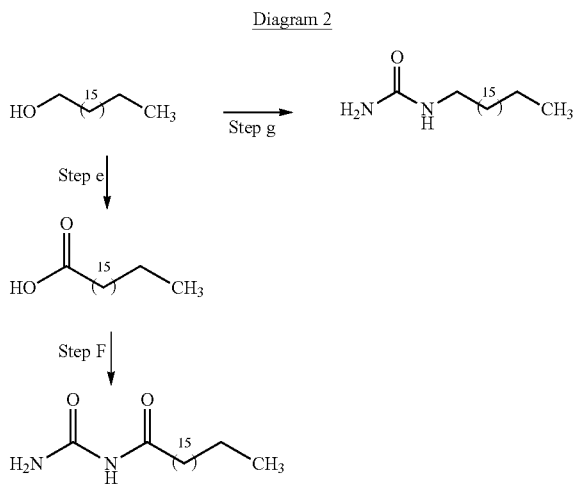

Diagram 2

In the first example, the hydroxyl group of the alcohol is oxidized (step (e)), using a suitable oxidizer such as potassium permanganate, to a carboxylate acid derivative, before heating the derivative intermediate, in a condensation reaction, in the presence of an equimolar amount of urea (step (f)) to produce a surfactant, which in this example is a urea pentadecanoic acid derivative.

In a second example (step (g)), the hydroxyl group of the alcohol is substituted for a urea moiety, in a condensation reaction, effected by heating the alcohol in the presence of an equimolar quantity of urea, to produce a surfactant without passing through a carboxylic acid intermediate as in the first example.

From the above, it is evident that a range of surfactants, for use in an emulsion explosive composition, can be manufactured from glycerol, with a range of carbon chain lengths (the hydrophobic part or tail group of the surfactant), providing a range of chemical and physical characteristics, and a variety of head groups (the hydrophilic part of the surfactant molecule), again providing a concomitant range of chemical and physical characteristics.

Diagram 3 illustrates the production of a polyol intermediate for the production of an explosive compound according to a second aspect of the invention.

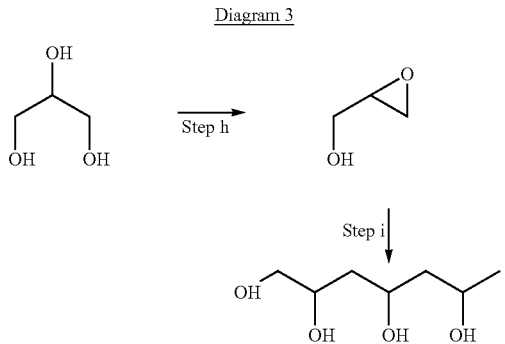

Diagram 3

In step (h), which includes the intermediate steps (a), (b) and (c) and which are not repeated here for the sake of simplicity of explanation, the glycerol is converted to glycidol. The polymerization step that follows (step (i)) produces a specific compound, a polyol intermediate, namely 1, 2, 4, 6 heptanetetraol.

The polyol intermediate product then undergoes an activation step (step (j)), illustrated in diagram 4, wherein each hydroxyl group, with the exception of the terminal hydroxyl group, is replaced, in this particular embodiment, by a chloride moiety. This is done by bubbling chloride gas through a solution of heptanetetraol. The intermediate product thereby formed, i.e. 2,4,6 trichloroheptane, is an oily compound that is inert and is therefore easily and safely transportable.

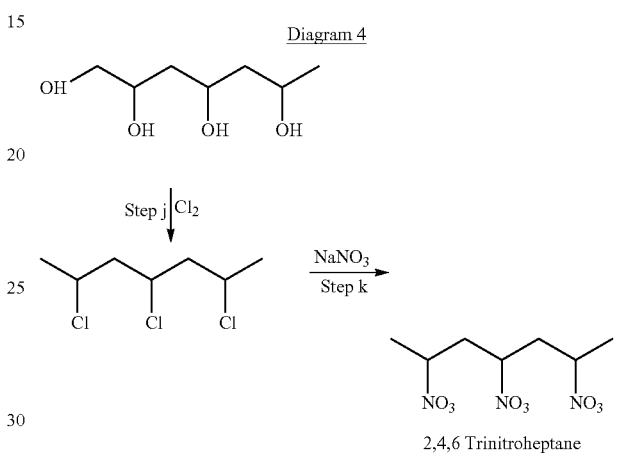

Diagram 4

2,4,6 Trinitroheptane

The final step, i.e. step (k), in the production of the explosive compound, takes place in situ. The trichloroheptane is transported to site and nitrated with sodium nitrate to produce 2,4,6 trinitroheptane, an explosive compound.

Some of the advantages of 2,4,6 trinitroheptane as an explosive and its production are:
- an increase in bulk strength;
- an increase in VOD and overall energy of the explosive reaction;
- the major phase, i.e. the trichloroheptane, is stable until sensitized;
- the major phase (trichloroheptane) will be non-detonable in bulk;
- the major phase is not flammable;
- a cost reduction in the production of the explosive as production is decoupled from current fuel prices and the cost and availability of ammonium nitrate;
- glycerol, as a waste product generated by the bio-fuel industry, is used, an environmental advantage;
- the sensitivity of the explosive compound is increased over state of the art emulsion explosives; and
- sensitization of the product occurs in situ i.e. in the hole.

The invention claimed is:

1. A method of producing a surfactant from glycerol which includes the steps of:
   (a) converting glycerol to glycidol,
   (b) polymerizing glycidol to produce an aliphatic alcohol with molecular formula $C_nH_{(2n)}O$, wherein n is a numerical integer in the range 5 to 25; and
   (c) substituting the hydroxyl moiety of the alcohol with a suitable head group.

2. A method according to claim 1 wherein the conversion of glycerol to glycidol includes the additional steps of dehydrating glycerol to acrolein (propenal), hydrogenating acrolein to allyl alcohol and epoxidizing allyl alcohol, with hydrogen peroxide, to glycidol.

3. A method according to claim 2 wherein a zeolite based catalyst is used in the dehydration step.

4. A method according to claim 2 wherein a hydrogenating catalyst, including a support and at least one transition metal on the support, is used in the hydrogenation step.

5. A method according to claim 4 wherein the at least one transition metal is cadmium, silver or iron.

6. A method according to claim 2 wherein an epoxidizing catalyst, selected from the group consisting of a titanium molecular sieve and a gold containing catalyst, is used in the epoxidizing step.

7. A method according to claim 1 wherein polymerization, in step (b), takes place by heating glycidol, in an acidic medium, for a predetermined period, the length of which is dependent upon the number of carbon atoms (n) required in a tail group of the surfactant.

8. A method according to claim 7 wherein the polymerization step is initiated with boron triflouride.

9. A method according to claim 7 wherein the tail group has a length in a range n=10 to 20.

10. A method according to claim 1 wherein the head group is an anionic moiety.

11. A method according to claim 10 wherein the anionic moiety is selected from the group consisting of: a carboxylate, a sulphate, a sulphonate, a phosphate and salts thereof.

12. A method according to claim 1 wherein the head group is a non-ionic moiety.

13. A method according to claim 7 wherein the non-ionic moiety is urea, MEA, an amide or an imide.

14. A method according to claim 13 wherein the urea moiety is substituted for the hydroxyl moiety in step (c) by heating the alcohol in the presence of an equimolar amount of urea.

15. A method of producing an explosive compound from glycerol which includes the steps of:
(a) converting glycerol to glycidol;
(b) polymerizing glycidol (the monomer) to produce an aliphatic polyol the polymer) with molecular formula $C_xH_{(2X+2)}O_y$, wherein X and Y are numerical integers in the range 3 to 30 and 3 to 15 respectively;
(c) activating the aliphatic polyol by substituting each of the hydroxyl moieties with a suitable leaving group to form an activated intermediate; and (d) nitrating the activated intermediate to substitute each of the leaving groups with a nitrate moiety to produce the explosive compound.

16. A method according to claim 15 wherein the aliphatic polyol is 1,2,4,6 heptanetetrol ($C_7H_{16}O_4$).

17. A method according to claim 15 wherein the leaving group is selected from the group consisting of: chloride, iodide, bromide, azide ($N_3^-$), thiocyanate ($SCN^-$) and nitro ($NO_2$).

18. A method according to claim 17 wherein the leaving group is a chloride ion and the aliphatic polyol is activated with chloride by bubbling chlorine gas through a solution of the polyol in a chlorination process.

19. A method according to claim 18 wherein the activated intermediate is 2,4,6 trichloroheptane.

20. A method according to claim 15 wherein the nitration step (d) includes the addition of a nitrate salt to the activated intermediate.

21. A method according to claim 15 wherein the explosive compound is 2,4,6 trinitroheptane.

* * * * *